United States Patent
Therre et al.

(10) Patent No.: US 6,175,044 B1
(45) Date of Patent: Jan. 16, 2001

(54) PREPARATION OF CITRAL

(75) Inventors: Jörg Therre, Worms; Gerd Kaibel, Lampertheim; Werner Aquila, Mannheim; Günter Wegner, Römerberg; Hartwig Fuchs, Ludwigshafen, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/404,548

(22) Filed: Sep. 24, 1999

(30) Foreign Application Priority Data

Oct. 7, 1998 (DE) .............................. 198 46 056

(51) Int. Cl.$^7$ .............................. C07C 45/51; C07C 47/21
(52) U.S. Cl. .......................... 568/486; 568/460; 568/458; 568/459
(58) Field of Search ..................... 568/449, 460, 568/450, 448, 459, 486

(56) References Cited

U.S. PATENT DOCUMENTS

| | | | |
|---|---|---|---|
| 4,016,212 | 4/1977 | Leimgruber et al. | 260/614 R |
| 4,288,636 | 9/1981 | Nissen et al. | 568/486 |
| 5,177,265 * | 1/1993 | Chabardes et al. | 568/460 |

FOREIGN PATENT DOCUMENTS

| | | |
|---|---|---|
| 2 411 530 | 9/1974 | (DE) . |
| 0 021 074 | 1/1981 | (EP) . |

* cited by examiner

Primary Examiner—Sreeni Padmanabhan
(74) Attorney, Agent, or Firm—Oblon, Spivak, McClelland, Maier & Neustadt, P.C.

(57) ABSTRACT

3,7-Dimethyl-2,6-octadien-1-al of formula I is prepared continuously by:

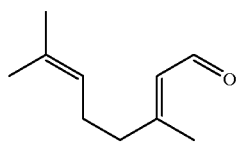

(I)

thermally cleaving, in the presence or absence of an acid catalyst, 3-methyl-2-buten-1-al diprenyl acetal of formula II:

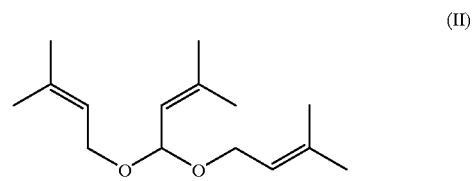

(II)

thereby eliminating 3-methyl-2-buten-1-ol of formula III and yielding cis/trans-prenyl 3-methylbutadienyl ether of formula IV:

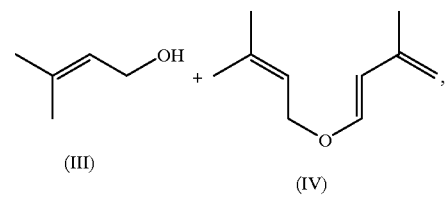

(III)          (IV)

thermally rearranging the resultant butadienyl ether of formula IV thereby yielding 2,4,4-trimethyl-3-formyl-1,5-hexadiene of formula V:

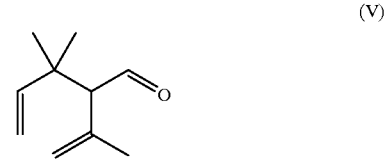

(V)

subsequently rearranging intermediate (V) thereby yielding citral product of formula I, which comprises:

as the reaction proceeds, continuously distilling the reaction mixture thereby continuously removing prenol, which is formed by degradation of acetal II, and the intermediates of formula IV and V and any citral product which is formed during the reaction; and thermally rearranging said intermediates of formula IV and V at a temperature of 100–200° C. in the absence or presence of said prenol to form citral product.

10 Claims, 1 Drawing Sheet

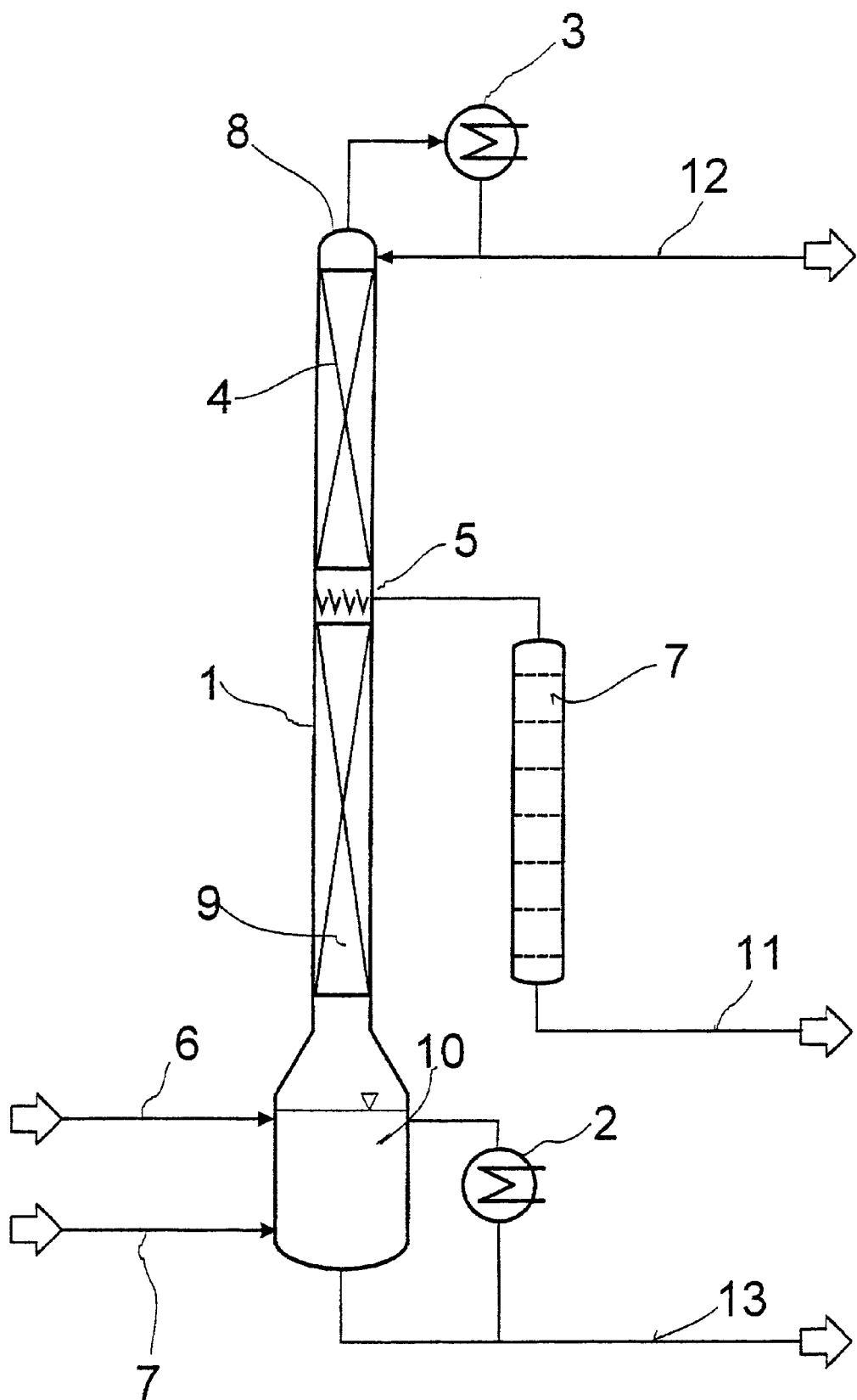

PREPARATION OF CITRAL

BACKGROUND OF THE INVENTION

1. Field of the Invention

The present invention relates to an improved process for preparing 3,7-dimethyl-2,6-octadien-1-al (citral) by thermal cleavage of 3-methyl-2-buten-1-al diprenyl acetal.

2. Description of the Background

Disregarding the improvements according to the invention, this reaction has already been disclosed in its essential features, Inter alia, by DE 24 11 530 and EP 210 074 B1.

This is a highly complex reaction which proceeds via three stages, as follows from the reaction diagram below.

1. Thermal cleavage of the acetal of the formula II into 3-methyl-2-buten-1-ol (prenol) of the formula III and the cis/trans-prenyl 3-methylbutadienyl ether (dienyl ether) of the formula IV

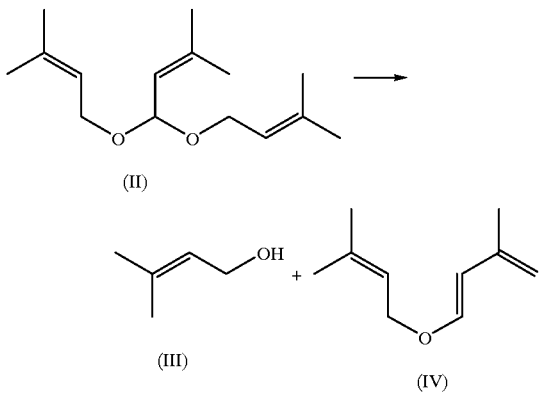

2. Thermal rearrangement of the dienyl ether of the formula IV in a Claisen rearrangement to give 2,4,4-trimethyl-3-formyl-1,5-hexadiene (formylhexadiene) of the formula V

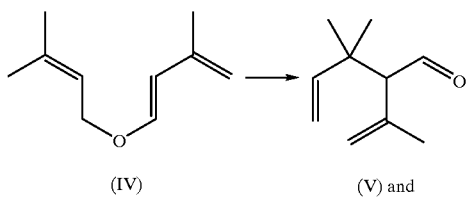

3. Thermal rearrangement of the dienyl ether of the formula V in a Cope rearrangement to give the desired citral of the formula I

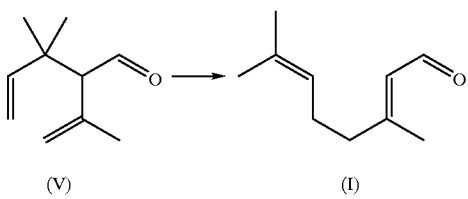

Citral is used as a scent and, furthermore, is of great importance as a starting material for other scents, such as geraniol, and as a starting material for vitamins, for example vitamin A.

Since not only the starting compound of the formula II but also the desired citral, the byproduct prenol and the citral precursors of the formulae IV and V are sensitive substances which can react further in an undesirable manner, the preparation of citral initially succeeded only with yields of from 60 to 70%. Better citral yields by far were obtained, even on an industrial scale, in accordance with the process of EP 0 021 074 B1. This describes a process for preparing citral from the acetal of the formula II, which comprises continuously distilling off from the reaction mixture, during the reaction, the prenol formed as byproduct. The citral and the citral precursors of the formulae IV and V are retained in the reaction mixture in this case by a distillation tower. The continuous removal of the prenol from the reaction mixture increased the citral yield to about from 85 to 90%. To increase the citral yield further, in EP 0 021 074, in addition, the conjoint use of a substance having a boiling point between that of prenol and that of citral and the citral precursors of the formulae IV and V (what is termed the intermediate boiler) was recommended. This measure increased the citral yield to approximately 95% of theory.

A disadvantage of the process described, which is very good per se, is that the process is only suitable for a batchwise procedure and requires long residence times (about 6 hours) and therefore large apparatuses. A further disadvantage of the known process is that an auxiliary, that is to say the intermediate boiler, must be introduced into the system, which means additional resources for metering the auxiliary, for monitoring its concentration and removing it.

SUMMARY OF THE INVENTION

It is an object of the present invention, therefore, to improve the process for preparing citral by thermal cleavage of the acetal of the formula II in such a manner that the abovedescribed disadvantages are avoided. This meant improving the process in such a manner that the use of auxiliaries is not necessary, so that shorter residence times and therefore small apparatuses can be employed, but nevertheless high selectivities for citral are achieved.

We have found that this object is achieved, therefore, by a process for preparing 3,7-dimethyl-2,6-octadien-1-al (citral) of the formula I

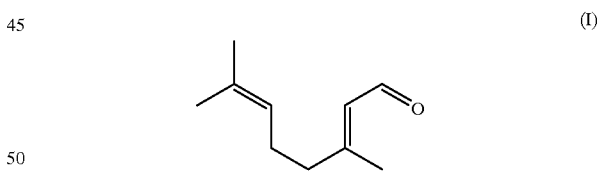

by thermal cleavage, in the presence or absence of an acid catalyst, of 3-methyl-2-buten-1-al diprenyl acetal of the formula II

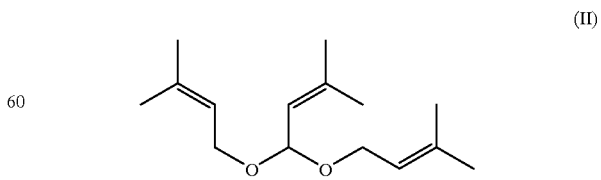

with elimination of 3-methyl-2-buten-1-ol (prenol) of the formula III to give cis/trans-prenyl 3-methylbutadienyl ether of the formula IV

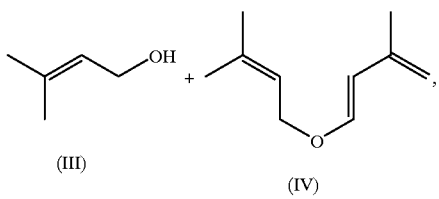

(III)  (IV)

Claisen rearrangement of the resultant butadienyl ether of the formula IV to give 2,4,4-trimethyl-3-formyl-1,5-hexadiene of the formula V

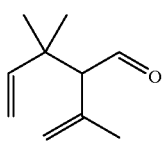

(V)

and subsequent Cope rearrangement of the same to give citral of the formula I,
which comprises continuously removing by distillation from the reaction mixture not only the prenol formed of the formula III, but also the intermediates of the formulae IV and V and the citral, even during the reaction, and rearranging the intermediates of the formulae IV and V by heating them to from 100 to 200° C. to form citral before or after removal of prenol and possibly byproducts by distillation.

DETAILED DESCRIPTION OF THE PREFERRED EMBODIMENTS

The process according to the invention succeeds particularly advantageously if the thermal cleavage of the acetal of the formula II is carried out in the lower part or in the bottom of a distillation tower which is acting as a cleavage tower and has from 5 to 100 theoretical plates.

In this case, it has proved to be highly expedient if the acetal of the formula II, with or without the acid catalyst, is introduced into the lower part of the tower, into the bottom of the tower or into the tower evaporator (2).

One possible method for carrying out the process according to the invention comprises carrying out the thermal cleavage of the acetal of the formula II in the lower part or in the bottom of a distillation tower having from 5 to 100 theoretical plates, the acetal of the formula II being kept by suitable choice of the distillation conditions in the lower part, or in the bottom, of the tower, the citral formed of the formula I, the intermediates formed of the formulae IV and V and the eliminated prenol of the formula III being produced jointly at the top of the tower as overhead stream and the mixture of citral and the intermediates of the formulae IV and V, before or after removing prenol, and possibly byproducts, by distillation, then being passed through a heated delay tube (7) in which the intermediates of the formulae IV and V are rearranged at from 100 to 200° C. to give citral. Particularly advantageously, the process according to the invention is arranged in such a manner that the thermal cleavage of the acetal of the formula II is carried out in the lower part (9) or in the bottom (10) of a distillation tower (1) having from 5 to 100 theoretical plates, the acetal of the formula II being kept in the lower part (9) or in the bottom (10) of the tower (1) by suitable choice of the distillation conditions, the citral formed of the formula I and the intermediates formed of the formulae IV and V being taken off together in the liquid state or vapor state at a sidestream takeoff (5) disposed in the central or lower part of the tower and the prenol eliminated of the formula III being separated off at the head (8) of the tower with the overhead stream.

The mixture produced of citral and the intermediates of the formulae IV and V which is taken off at the sidestream takeoff (5) or else from the overhead stream of a tower without a sidestream takeoff is then expediently passed through a heated delay tube (7) in which the intermediates of the formulae IV and V are rearranged to form citral at temperatures of from 100 to 200° C.

The acetal required as starting compound can, as described in EP 0 021 074 B1, for example, be prepared very simply by reacting 3-methyl-2-buten-1-ol (prenol) with 3-methyl-2-buten-1-al (prenal). Depending on the acetal preparation conditions, this can comprise from 0.1 to 30% by weight of unreacted prenal and from 0.1 to 60% by weight of unreacted prenol. It is advantageous for the process according to the invention if the concentration of the acetal of the formula II used is over 30% by weight, preferably over 70% by weight in the starting material.

The preferred procedure of the process according to the invention is described below on the basis of the accompanying figure:

BRIEF DESCRIPTION OF THE DRAWINGS

The acetal of the formula II is cleaved to form prenol, citral and the citral precursors of the formulae IV and V in a distillation tower, termed the cleavage tower (1), which is equipped with an evaporator (2) and a condenser (3). Suitable internals (4) for the tower are plates, dumped packings and, in particular, arranged packings of sheet metal (e.g. Sulzer 250.Y) or metal cloth (e.g. Sulzer BX or Sulzer CY). The number of theoretical plates of the tower is to be from 5 to 100. In a preferred embodiment of the invention, a sidestream takeoff (5) is present from which the citral and the citral precursors are taken off from the tower in vaporous or liquid form. The sidestream takeoff (5) is situated in the central or lower part of the tower (1), the sidestream takeoff (5) being expediently situated from 2 to 20 theoretical plates above the feed point (6) of the acetal. A further from 2 to 80 theoretical plates are situated above the sidestream takeoff (5). The mixture of citral and the citral precursors is passed through a heated delay tube (7), in which the citral precursors of the formulae IV and V are thermally converted to form citral. The citral produced can then be taken off at the takeoff point (11).

The prenol with or without 3-methyl-2-buten-1-al recovered from the overhead stream in the condenser (3) can be taken off at the takeoff point (12) and recirculated back into the process for preparing the acetal of the formula II. The relatively small amounts of bottom discharge arising in the process can be taken off at the takeoff point (13).

The acetal is added in the lower part of the cleavage tower (1), but preferably in the bottom (10) of the cleavage tower (1) or in the evaporator (2). The bottom (10) of the cleavage tower can be enlarged by a vessel in order to have a greater reaction volume available. The inflow of the acetal of the formula II is expediently dimensioned such that the residence time, based on the inflow of acetal, is from one minute to 6 hours, preferably from 5 minutes to 2 hours. This relatively short residence time and the small relatively inexpensive apparatuses enabled by this means represent a marked advantage of the process according to the invention.

The process can in principle be carried out batchwise, semicontinuously or continuously. For the semicontinuous procedure, at the start of the reaction a certain amount of acetal is charged and then further acetal can be added if necessary.

However, particularly advantageously, the process is carried out continuously.

If desired, to start up the apparatus, a high-boiling inert compound can be charged in the bottom of the tower, in order to ensure a minimum filling level of the bottom and of the evaporator. Suitable inert compounds are all liquid substances inert under the reaction conditions which have a boiling point higher than citral and, in particular, than that of the acetal of the formula II, such as the hydrocarbons tetradecane, pentadecane, hexadecane, octadecane, eicosane, or ethers, such as diethylene glycol dibutyl ether, white oils, paraffin oils or mixtures of said compounds.

The reaction can be carried out without catalyst, that is only by heating. However, particularly advantageously, it is carried out in the presence of an acid catalyst. Suitable acid catalysts in this case are, in particular, non-volatile proton acids such as sulfuric acid, p-toluenesulfonic acid and, especially, phosphoric acid.

The catalyst is advantageously added into the lower part of the cleavage tower (1), preferably into the bottom of the cleavage tower or into the evaporator (2).

The concentration of the catalyst in the reaction mixture is expediently from 0.0001% by weight to 1% by weight, preferably from 0.0005 to 0.5% by weight, based on the total amount of the reaction mixture. The catalyst can be added in pure form or dissolved in a suitable solvent. Suitable solvents for the catalyst are water, alcohols and hydrocarbons, but preferably the compounds present in the reaction mixture, such as prenol, 3-methyl-2-butenal, citral, the citral precursors of the formulae IV and V and, in particular, the acetal of the formula II. If water is used, its concentration in the reaction mixture is to be as low as possible, since water causes the back-reaction of the acetal to form prenol and 3-methyl-2-butenal. In the case of the other solvents, it is expedient if the concentration of the catalyst in the solvent is from 0.01% by weight to 50% by weight.

The pressure in the bottom of the cleavage tower is advantageously from 1 mbar to 100 mbar, in particular from 10 to 70 mbar. The temperature in the bottom of the tower is generally from 70° C. to 270° C., preferably from 100° C. to 220° C., in particular from 130° C. to 190° C.

The reflux ratio at the top of the cleavage tower is advantageously from 0.5 to 70, in particular from 2 to 30.

The amount of bottom discharge is extraordinarily low and is less than 10% by weight, frequently even less than 5% by weight, of the added acetal, since virtually all of the acetal of the formula II added is cleaved into products of value and only a very small part of the reactants react to form high-boiling byproducts. This high selectivity also represents a great advantage of the process according to the invention.

In the event that the cleavage tower possesses no sidestream takeoff, the distillate produced at the top of the tower essentially consists of the products of value prenol, 3-methyl-2-butenal, citral and the citral precursors of the formulae IV and V. This mixture can be separated in a simple manner by distillation, for example by distillation in a further tower, into prenol, with or without the unreacted 3-methyl-2-butenal originating from the preparation of the acetal of the formula II, and citral and the citral precursors of the formulae IV and V. It is also possible to rearrange the citral precursors present in this mixture to form citral by heating the mixture to temperatures from 100° C. to 200° C., then to separate off the citral by distillation. The recovered compounds prenol with or without 3-methyl-2-butenal can be reused for preparing the acetal of the formula II.

However, particularly advantageously, a cleavage tower having a sidestream takeoff is used to carry out the process according to the invention. In this case, an additional distillation tower can be omitted. The overhead takeoff of the cleavage tower then essentially consists of prenol with or without 3-methyl-2-butenal, which can be readily reused for preparing the acetal of the formula II. The product stream obtained via the sidestream takeoff consists of more than 70% by weight, and frequently even more than 85% by weight, of citral and the citral precursors of the formulae IV and V. The citral precursors present in this product stream are rearranged to form citral in a known manner by heating to temperatures from 100° C. to 200° C.

Using the process according to the invention it is possible to prepare citral, which is sought-after as a scent and as an intermediate for scents and vitamins, even on an industrial scale in a simple and inexpensive manner continuously and with excellent yields.

The examples below illustrate the invention.

EXAMPLES 1 TO 3

The apparatus consisted of an electrically heated 1 liter flask having an attached tower, which tower was equipped with an electric reflux divider (to achieve a reflux ratio of 1:1). The tower was packed with a 1-m-high Sulzer EX-packing. At the start of the experiment, the flask was filled with 500 g of a 90% strength by weight acetal of the formula II. In Examples 1 and 3, up to 31 ppm of phosphoric acid were added as catalyst. In Example 2, no catalyst was employed. The overhead pressure of the tower was from 5 to 60 mbar. After heating up the flask contents, from 100 g/h to 200 g/h of 3-methyl-2-butene diprenyl acetal were pumped in continuously. The cleavage products forming (principally prenol and the citral precursors cis/trans-prenyl 3-methylbutadienyl ether of the formula IV and 2,4,4-trimethyl-3-formyl-1,5-hexadiene of the formula V were distilled off continuously and collected. The acetal was retained by reflux and controlling the heat output in the reaction flask. After the end of the experiment, the distillate and the contents of the flask were weighed and analyzed by gas chromatography. The parameters and results of Examples 1 to 3 are summarized in Table 1.

TABLE 1

|  | Example 1 | Example 2 | Example 2 |
|---|---|---|---|
| Acetal feed rate [ml/h] | 100 | 100 | 200 |
| Pressure at top of tower [mbar] | 6 | 60 | 5 |
| Pressure in the flask [mbar] | 20 | 70 | 23 |
| Temperature in the flask [° C.] | 143 to 148 | 169 to 190 | 143 to 148 |
| Initial acetal weight [g] | 507.8 | 503 | 507.3 |
| Concentration of $H_3PO_4$ in the flask [ppm] | 31 | omitted | 27.2 |
| Acetal (filling + infeed) [g] | 891.3 | 1107.8 | 1485.2 |
| Amount of acetal fed in [g] | 383.5 | 604.8 | 977.9 |
| Distillate [g] | 711.9 | 958.4 | 1174.7 |
| Bottom phase at end of experiment [g] | 172.2 | 153.3 | 312.7 |
| Acetal conversion | 83.1% | 97.4% | 49.8% |
| Selectivity toward prenol | 98.7% | 95.2% | 92.7% |
| Selectivity toward citral and citral precursors | 89.1% | 96.0% | 97.8% |

EXAMPLES 4 TO 8

The parameters and results of Examples 4 to 8 are summarized in Table 2. The apparatus consisted of a cleavage tower having 30 theoretical plates. The bottom of the tower was heated by a falling-film evaporator. The sidestream takeoff for the citral and the citral precursors was situated 10 plates above the bottom. The distillate condensing at the top of the tower was collected and some of this was pumped as reflux back to the top of the tower. Per hour, 100 g of acetal of the formula II were added to the bottom of the tower. As catalyst, an approximately 1% strength by weight solution of H₃PO₄ in the acetal of the formula II was added to the bottom of the tower. The amount of catalyst solution was dimensioned in such a way that the concentration of H₃PO₄ in the bottom of the tower specified in the table was maintained. The selectivity toward prenol was greater than 89.3%.

TABLE 2

| Example | 4 | 5 | 6 | 7 | 8 |
|---|---|---|---|---|---|
| H₃PO₄ concentration [ppm] | 117 | 475 | 332 | 269 | 1044 |
| Temperature at the bottom [° C.] | 175 | 145 | 155 | 160 | 150 |
| Pressure at the tower top [mbar] | 50 | 30 | 30 | 30 | 50 |
| Reflux rate [g/h] | 968 | 774 | 968 | 774 | 774 |
| Acetal concentration in the infeed [kg/kg] | 83.94% | 76.93% | 76.93% | 88.25% | 85.82% |
| Bottom takeoff [g/h] | 0.37 | 33.51 | 6.82 | 0.51 | 6.91 |
| Sidestream takeoff [g/h] | 57.00 | 29.76 | 47.33 | 61.74 | 52.13 |
| Overhead takeoff [g/h] | 42.80 | 38.26 | 48.84 | 35.22 | 40.44 |
| Reflux ratio | 23 | 20 | 20 | 22 | 19 |
| Bottom-phase contents [g] | 100 | 100 | 100 | 170 | 170 |
| Acetal conversion | 99.5% | 67.5% | 95.3% | 99.8% | 99.3% |
| Selectivity toward citral and citral precursors | 91.8% | 96.6% | 90.0% | 93.4% | 97.6% |

We claim:

1. A process for continuously preparing 3,7-dimethyl-2,6-octadien-1-al of formula I by:

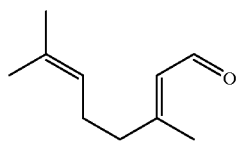

(I)

thermally cleaving, in the presence or absence of an acid catalyst, 3-methyl-2-buten-1-al diprenyl acetal of formula II:

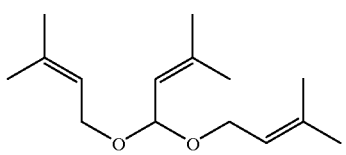

(II)

thereby eliminating 3-methyl-2-buten-1-ol of formula III and yielding cis/trans-prenyl 3-methylbutadienyl ether of formula IV:

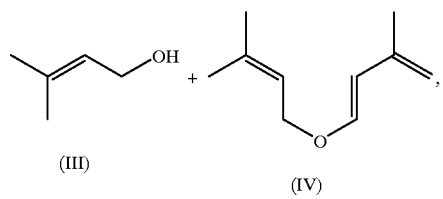

(III) (IV)

thermally rearranging the resultant butadienyl ether of formula IV thereby yielding 2,4,4-trimethyl-3-formyl-1,5-hexadiene of formula V:

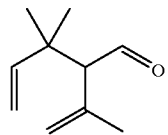

(V)

subsequently rearranging intermediate (V) thereby yielding citral product of formula I, which comprises:

as the reaction proceeds, continuously distilling the reaction mixture thereby continuously removing prenol, which is formed by degradation of acetal II, and the intermediates of formula IV and V and any citral product which is formed during the reaction; and thermally rearranging said intermediates of formula IV and V at a temperature of 100–200° C. in the absence or presence of said prenol to form citral product.

2. A process as claimed in claim 1, wherein the thermal cleavage of the acetal of the formula II is conducted in the lower part or in the bottom of a distillation tower having from 5 to 100 theoretical plates.

3. A process as claimed in claim 2, wherein the acetal of the formula II, with or without the acid catalyst, is introduced into the lower part of the tower, into the bottom of the tower or into the tower evaporator (2).

4. A process as claimed in claim 1, wherein the thermal cleavage of the acetal of the formula II is conducted in the lower part or in the bottom of a distillation tower having from 5 to 100 theoretical plates, the acetal of the formula II being kept by selection of distillation conditions in the lower part, or in the bottom, of the tower, the citral formed of the formula I, the intermediates formed of the formulae IV and V and the eliminated prenol of the formula III being removed together produced at the top of the tower as overhead stream and the mixture of citral and the intermediates of the formulae IV and V, before or after removing prenol, and byproducts, by distillation, then being passed through a heated delay tube (7) in which the intermediates of the formulae IV and V are rearranged at from 100 to 200° C. to give citral.

5. A process as claimed in claim 1, wherein the thermal cleavage of the acetal of the formula II is conducted in the lower part (9) or in the bottom (10) of a distillation tower (1) having from 5 to 100 theoretical plates, the acetal of the formula II being kept in the lower part (9) or in the bottom (10) of the tower (1) by selection of the distillation conditions, the citral formed of the formula I and the intermediates formed of the formulae IV and V being removed together in the liquid state or vapor state at a sidestream takeoff (5) disposed in the central part of the tower and the prenol eliminated of the formula III being separated off at the top (8) of the tower with the overhead stream.

6. A process as claimed in claim 5, wherein the mixture of citral and the intermediates formed of the formulae IV and V which is removed at the sidestream takeoff (5) is passed through a heated delay tube (7) in which the intermediates of the formulae IV and V are rearranged to form citral at a temperature from 100 to 200° C.

7. A process as claimed in claim 5, wherein citral is prepared continuously.

8. A process as claimed in claim 5, wherein the sidestream takeoff (5) is situated from 2 to 20 theoretical plates above the feed point (6) for the acetal of the formula II and from 2 to 80 theoretical plates below the tower top (8).

9. A process as claimed in claim 2, wherein the pressure in the bottom of the tower ranges from 1 to 100 mbar and the temperature in the bottom of the tower ranges from 70 to 270° C.

10. A process as claimed in claim 2, wherein the reflux ratio at the top of the distillation tower ranges from 0.5 to 70.

* * * * *